(12) United States Patent
Buchanan

(10) Patent No.: US 7,942,673 B2
(45) Date of Patent: May 17, 2011

(54) DENTAL OBTURATOR

(76) Inventor: L. Stephen Buchanan, Santa Barbara, CA (US)

( * ) Notice: Subject to any disclaimer, the term of this patent is extended or adjusted under 35 U.S.C. 154(b) by 911 days.

(21) Appl. No.: 11/663,416

(22) PCT Filed: Sep. 7, 2004

(86) PCT No.: PCT/US2004/029434
§ 371 (c)(1),
(2), (4) Date: Mar. 20, 2007

(87) PCT Pub. No.: WO2005/023132
PCT Pub. Date: Mar. 17, 2005

(65) Prior Publication Data
US 2008/0014554 A1    Jan. 17, 2008

Related U.S. Application Data

(60) Provisional application No. 60/500,623, filed on Sep. 5, 2003.

(51) Int. Cl.
*A61C 5/02* (2006.01)
*A61G 5/02* (2006.01)

(52) U.S. Cl. ........................................ 433/224; 433/102

(58) Field of Classification Search .................... 433/81, 433/83, 102, 221, 224; 604/104–109, 164.01, 604/164.03, 170.01–170.03, 264, 272–274; 606/167, 185, 188

See application file for complete search history.

(56) References Cited

U.S. PATENT DOCUMENTS

| | | | |
|---|---|---|---|
| 1,694,857 A | | 12/1928 | Kulick |
| 4,758,156 A | * | 7/1988 | Johnson .......................... 433/81 |
| 5,104,316 A | * | 4/1992 | McSpadden .................. 433/102 |
| 5,118,297 A | | 6/1992 | Johnson |
| 5,257,934 A | | 11/1993 | Cossellu |
| 5,662,607 A | * | 9/1997 | Booth et al. ............. 604/103.03 |
| 5,833,457 A | * | 11/1998 | Johnson .......................... 433/81 |
| 5,857,852 A | * | 1/1999 | Garman ........................ 433/102 |

FOREIGN PATENT DOCUMENTS

WO    WO03011154    *    2/2003

* cited by examiner

*Primary Examiner* — Cris L Rodriguez
*Assistant Examiner* — Matthew M Nelson
(74) *Attorney, Agent, or Firm* — Koppel, Patrick, Heybl & Philpott; Michael J. Ram

(57) ABSTRACT

Dental obturators are used in the preparation of root canals in teeth. The subject obturators are so constructed that they bind at a particular distance into the canal, thereby precluding possible damage at the end of the canal. The obturator is used for positioning of a sealing material placed on a carrier portion of the obturator into the root canal. Disclosed are a variety of structural configurations on a tapered surface of the carrier portion is disclosed.

18 Claims, 7 Drawing Sheets

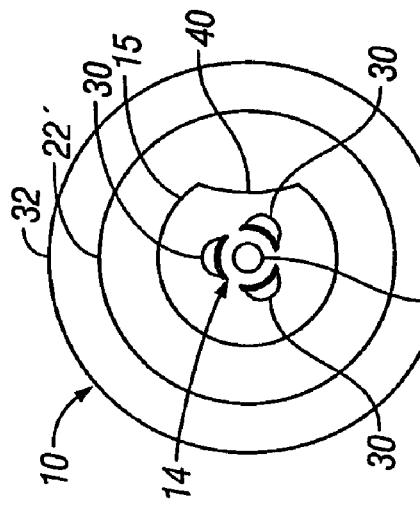
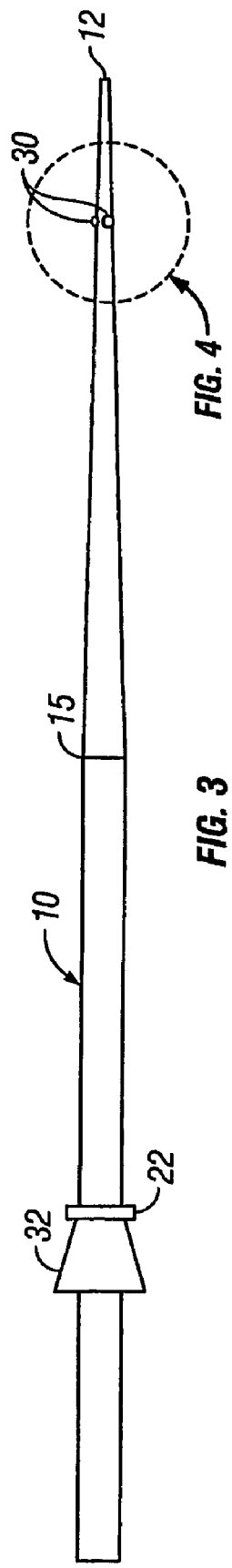
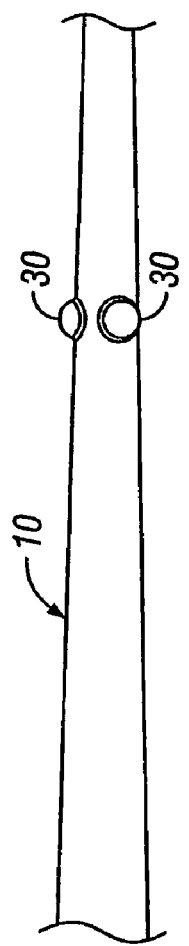

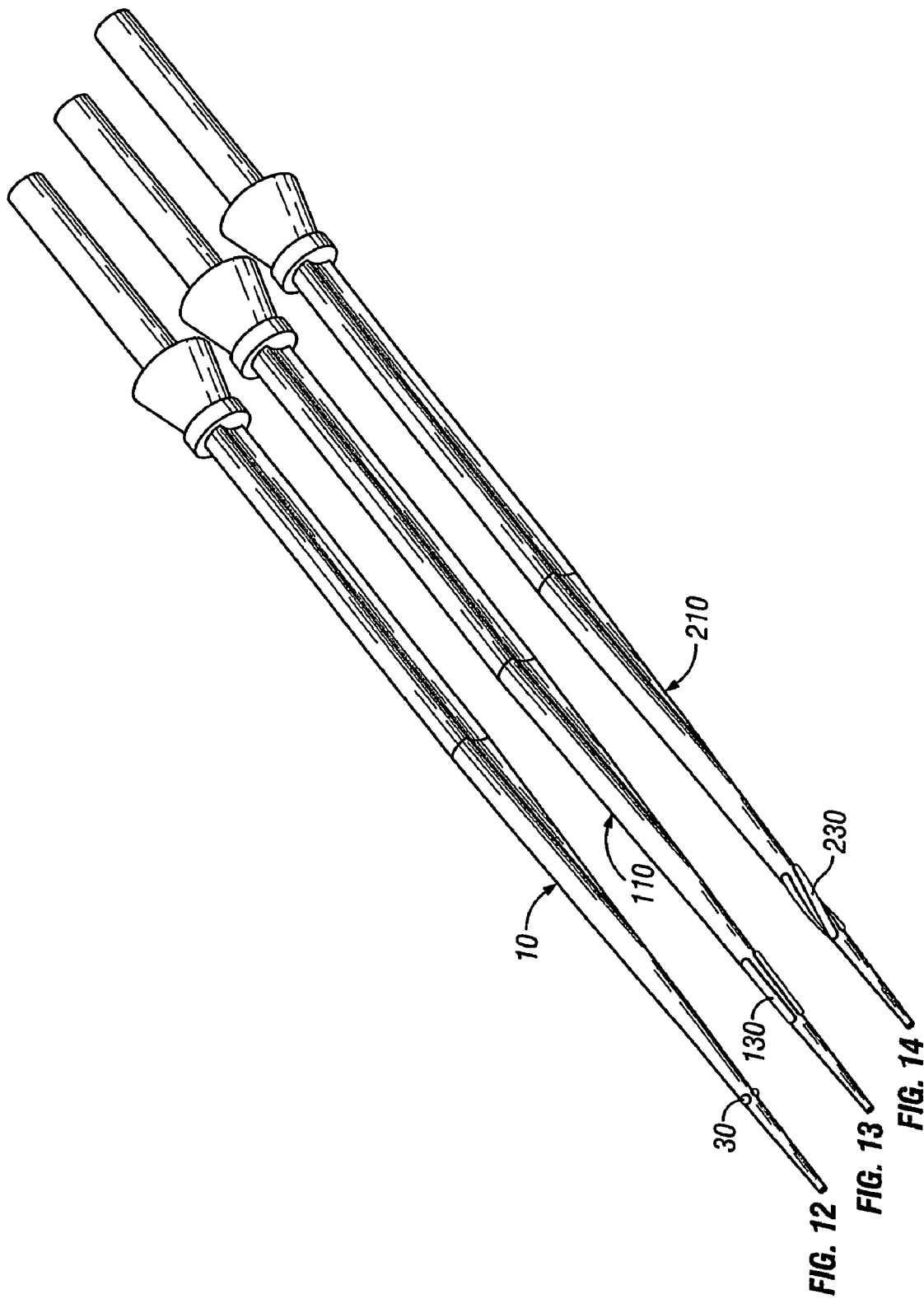

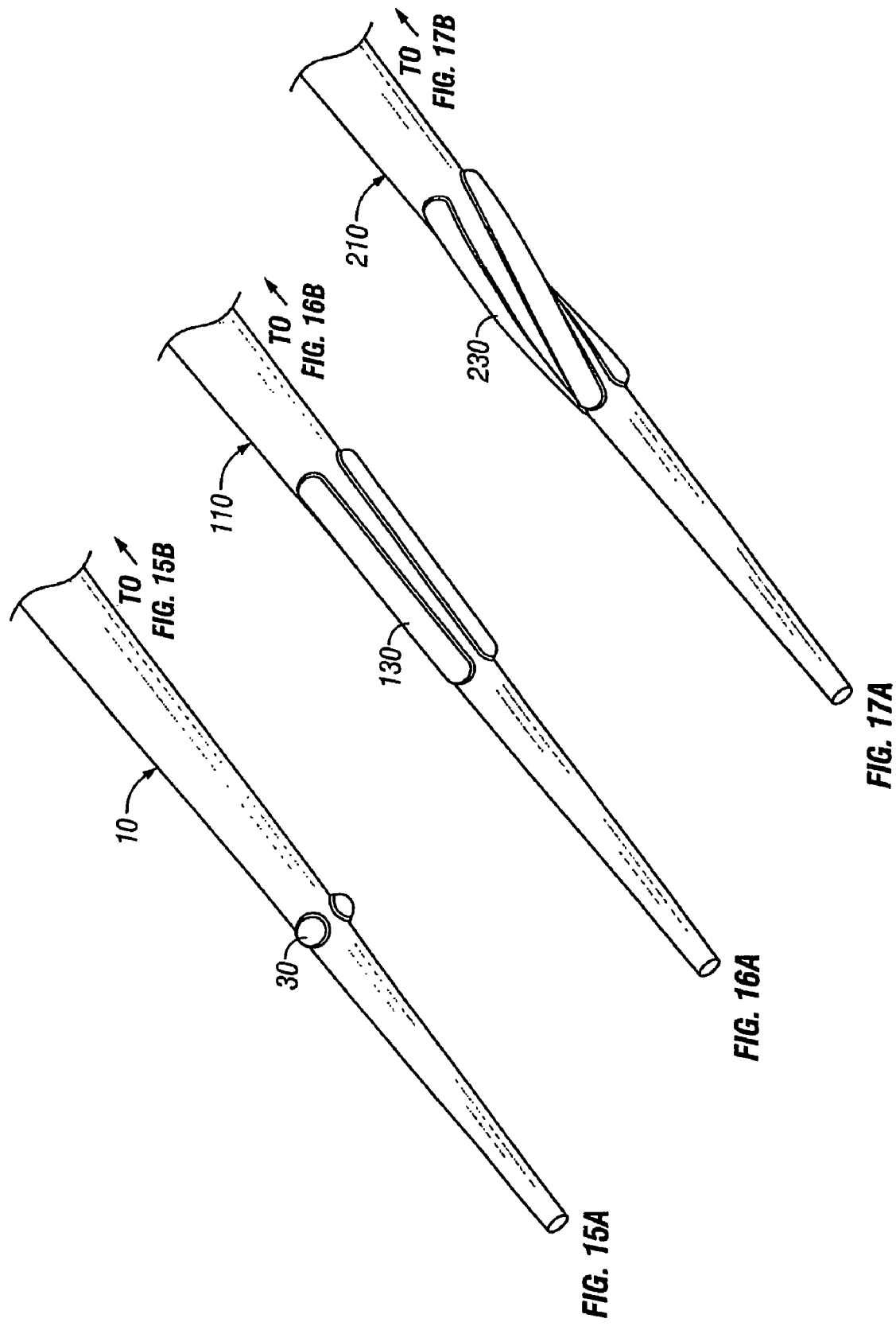

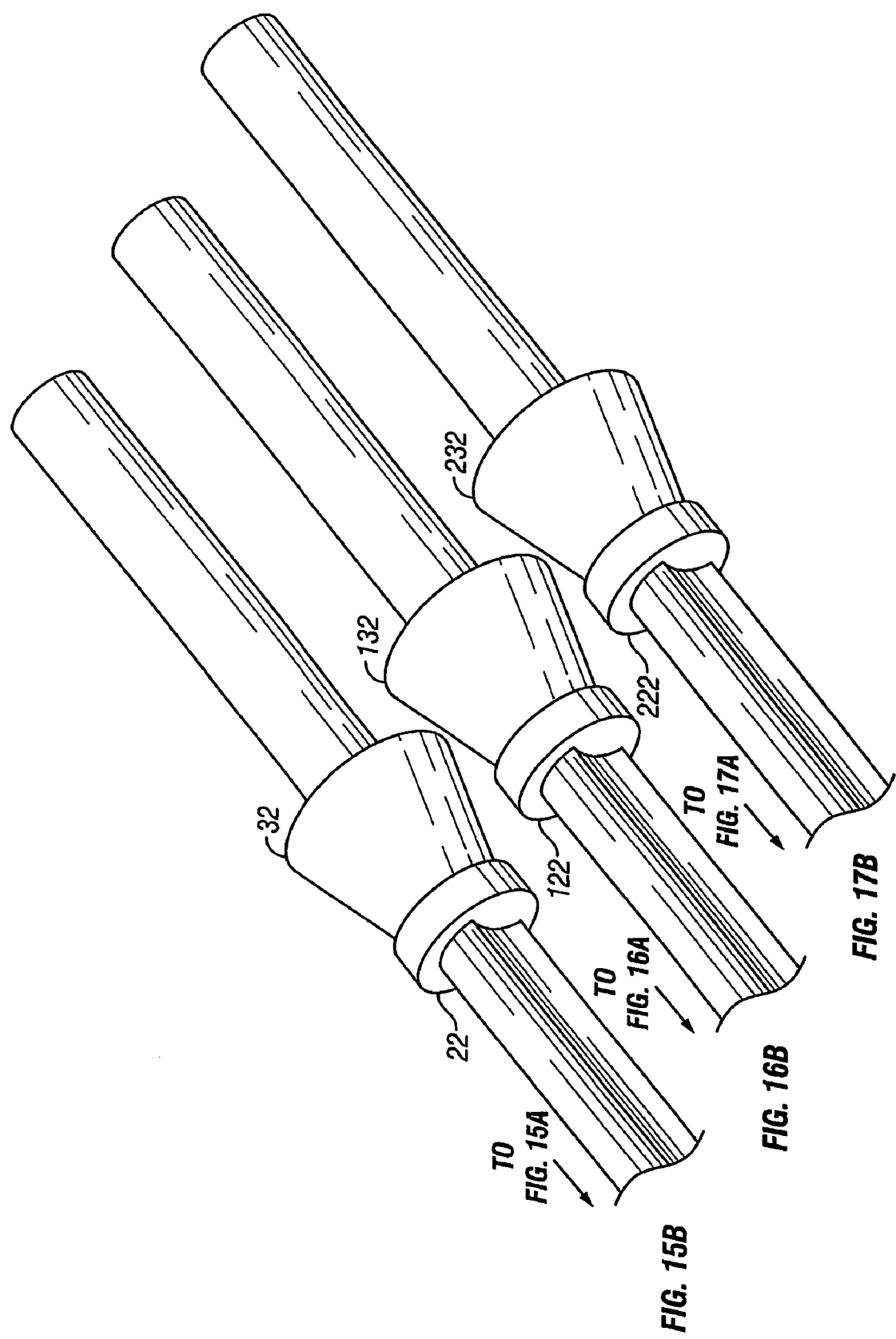

DENTAL OBTURATOR

CROSS-REFERENCE TO RELATED APPLICATION

This application claims priority from International Application No. PCT/US2004/029434, filed Sep. 7, 2004, and U.S. Provisional Application Ser. No. 60/500,623, filed Sep. 5, 2003.

BACKGROUND OF THE INVENTION

1. Field of the Invention

This invention relates to dental implements and, more particularly to such implements which are particularly designed for the filling of root canals with sealing materials.

2. Description of the Related Art

Dental obturators, often referred to as pluggers or, if provided with heating elements, heat carrier/pluggers, are design d for the insertion and packing of tapered gutta percha cones into a previously prepared root canal. My U.S. Pat. No. 5,921,775, describes ar endodontic treatment system in which the shaping instruments, irrigation cannulas, filling implements and related materials designed to safely create specific tapers in root canal preparation are provided. All of these various implements are designed with the same taper, preferably one which is greater than the standard ISO taper of 0.02 mm of taper/mm of flute length. My patent describes some of the benefits to be realized from using a taper which is greater than the 0.02 taper (the ISO standard) and also benefits derived from having all of the files and auxiliary implements with the same taper.

In the preparation of a root canal by removing the pulp and shaping the canal to the best configuration for receiving filling materials, such as gutta percha, it is extremely important to control the depth of penetration of root canal files and to limit the depth of penetration to the root tip. In one procedure known in the prior art, as disclosed in U.S. Pat. No. 4,028,810 of Vice, the length of the tooth involved, as well as the length of the root canal, is accurately determined by means of X-rays.

Negotiation files may be used to keep track of the depth of the root tip as the root canal is being enlarged and shaped in preparation for the final step of insertion of the filling material. Various methods are used to limit the depth of penetration to a safe degree. Extreme care must be taken to avoid penetration beyond the root canal which may result in injury and possible infection of the adjacent periodontal tissue and bone structure.

U.S. Pat. No. 4,028,810 of Vice also discloses a handle portion which is adjustably mounted in telescoping relation on the shaft of an elongated working tool. This arrangement provides a means for quickly and accurately adjusting the working length of the tool projecting from the handle.

U.S. Pat. No. 3,911,587 of Forrest et al. discloses the use of reference devices formed with a plurality of blind bores of predetermined depth. These cover the known range of root canal depths, and permit the insertion of an instrument to be used in the procedure by setting the marker on the instrument.

U.S. Pat. No. 4,165,562 of Sarfatti discloses a base and sleeve jointly provided with mating threads to facilitate precise longitudinal adjustment of the file relative to the sleeve. The bottom end of the sleeve is utilized as a stop which abuts the tooth to thereby limit the depth of file penetration.

These and other prior art devices of similar design have a number of disadvantages in use. They are somewhat cumbersome in construction and it is time-consuming to use such that occasionally an endodontist will bypass the step of using such an implement, and work on the root canal directly with the preparation file, sometimes with disastrous results.

SUMMARY OF THE INVENTION

In brief, particular arrangements in accordance with the present invention present a new design concept which serves to make the handling, placement and accuracy in use of the GT Obturators easier for clinicians while chairside. The efficiency which is gained and the integral design of the carrier also allow for more work to be completed within the same appointment. GT Obturators in accordance with the invention are designed to be used in root canal shapes that are created with GT files specified in my U.S. Pat. No. 5,921,775 which establish a predefined tapered shape within the canal.

The obturators of the invention have specific structural configurations which have one or more projections from the surface of the carrier that stop the insertion of the carrier at a point which is back from the end of the tapered canal. In one such arrangement, these projections are in the form of auto-stop carrier bumps located 3 mm back from the tip of the carrier. The projections are mounted on the carrier surface on three sides, all at the same 3 mm distance from the tip. In the predefined shape created by GT files, the bumps are sized to automatically bind the canal wall when the tip of the carrier is exactly 1 mm from the canal terminus. A number of advantages are gained from this design.

One of the more important advantages is the ease of use, as the carriers no longer need to be measured or the stops adjusted prior to placement in the heating oven for the gutta percha filling material. The carrier can literally be taken out of its package, heated, and then placed in the tooth.

As another advantage from use of this automatic stop, the clinician is eliminated as a variable in apical accuracy in filling the canal. In other words, the variations in clinicians abilities to place the carrier accurately have been leveled.

As a further benefit, since the carrier is unable to move apically regardless of the force placed on it, a post space can now be drilled through the coronal portion of the carrier in the same dentist visit. Previously known designs required a second visit after the sealer and gutta percha are fully set to hold the carrier in place. Cutting a post space with a post space drill prior to gutta percha and sealer setting often results in over-insertion of the carrier and the expulsion of unnecessary surplus of filling material beyond the terminus of the root canal.

In another particular arrangement in accordance with the invention, the diameter of the carrier handle which is provided is dramatically reduced in size. Handles which are currently in use are difficult for an assistant to grasp with locking cotton pliers which are used in passing the heated carrier to the doctor for placement in the canal. With the reduction in diameter of carries handles in accordance with the invention, the handles are much easier to grasp with cotton pliers. Also the smaller handles significantly increase the doctor's visibility of the access cavity during placement of the carrier, as opposed to the doctor having to look around his fingers which fill the operative field of view. Furthermore, in multi-canal teeth, it is difficult to place two carriers, with their handles side by side, and it is impossible to place more than two carriers without cutting the handles off.

In summary, by use of the improved arrangements in accordance with the present invention the placement and packing of the filling material can be accomplished in half the time formerly required to fill with carriers, and without requiring a costly second appointment in cases where a post space is needed. Use of arrangements of the present invention also provide the benefits of eliminating filling length errors, and allow multiple carriers to be placed in a tooth, one after another, before cutting them all in one cutting operation. As a result, dentists are able to concentrate more on the task and less on their techniques.

In one specific embodiment of the invention, the surface projections are in the general form of partial spheres installed on the outer surface of the carrier, preferably at a distance of one-third the carrier length from the tip. These surface projections ("bumps") are situated in groups of three, spaced approximately equidistant about the circumference of the carrier and all at the same distance from the tip. The center of each transverse bump is located on the outer diameter of the carrier. The diameter of each spherical projection is preferably ¼ of the carrier diameter at the location of the bumps.

In another particular embodiment of the invention, the projections are in the form of spaced-apart ridges, again mounted generally equidistant about the circumference of the carrier. As a variation on this embodiment, the ridges may be arranged in a spiral configuration. The advantage of using the ridged embodiment is that it provides some leeway in the insertion of the carrier into the root canal. The spiral ridge embodiment, in particular, also provides a better support for the filling material to be held along the carrier.

In these embodiments of the invention, it is preferred that the carrier is bare for the final 1.5 mm of its length. This means that the filling material does not extend along the last 1.5 mm from the tip. As a result, gutta percha removal is not required at the tip as contrasted with present practice where the gutta percha extends beyond the tip and must be trimmed before use.

BRIEF DESCRIPTION OF THE DRAWINGS

A better understanding of the present invention may be realized from a consideration of the following detailed description, taken in conjunction with the accompanying drawings, in which:

FIG. 3 is a schematic side view of one particular carrier in accordance with the invention;

FIG. 4 is an enlarged view of a portion of the carrier of FIG. 3;

FIG. 5 is a schematic view of the carrier of FIG. 3, viewed from the right-hand end;

FIG. 12 is a simulated photograph of the carrier of FIG. 3;

FIG. 13 is a simulated photograph of the carrier of FIG. 6;

FIG. 14 is a simulated photograph of the carrier of FIG. 9; and

FIGS. 15A and 15B, 16A and 16B, and 17A and 17B are enlarged views of the carriers of FIGS. 12, 13 and 14, respectively.

DESCRIPTION OF THE PREFERRED EMBODIMENTS

Figure 1:
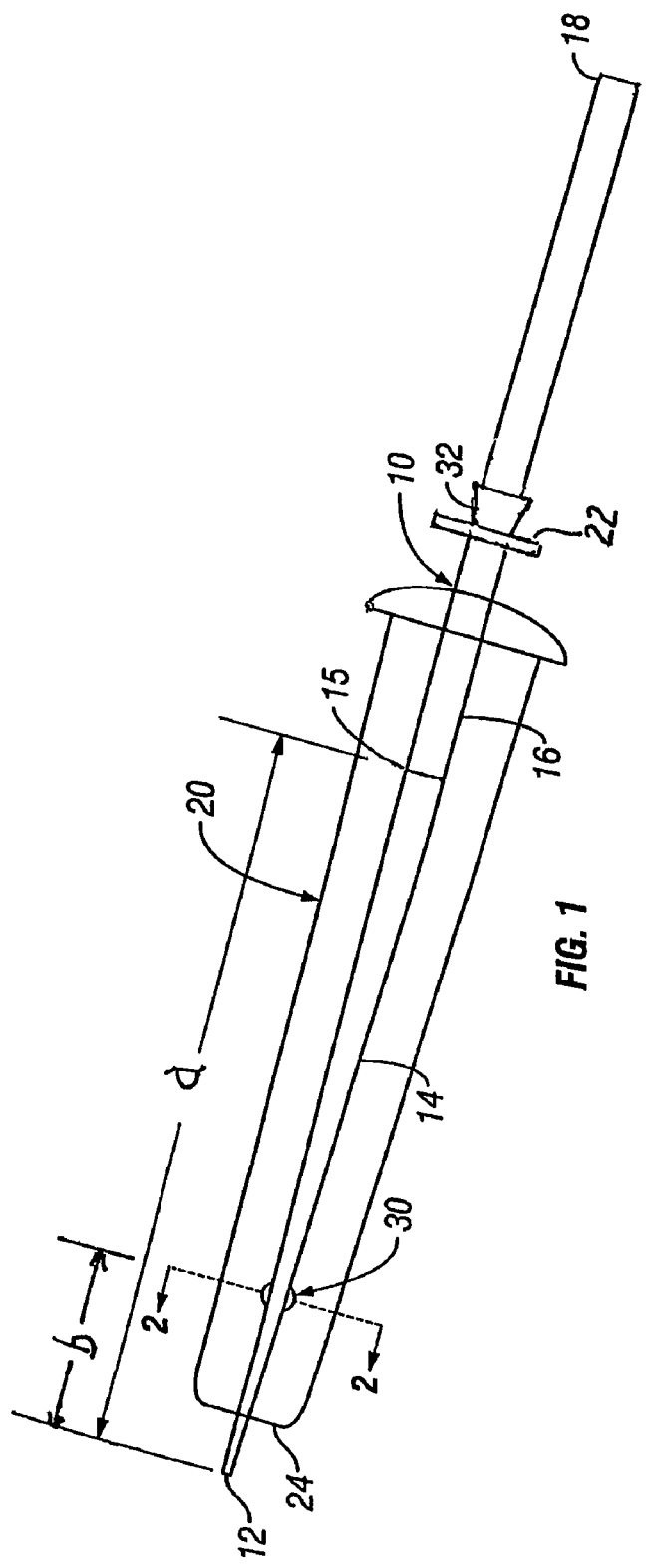
FIG. 1 is a schematic view showing a carrier/obturator in accordance with the present invention.
Figure 2:
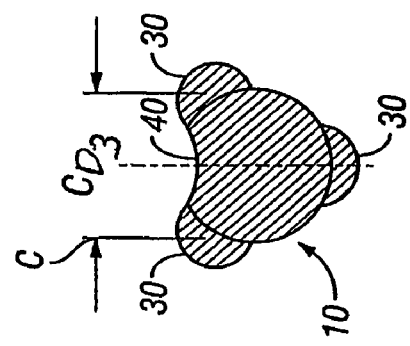
FIG. 2 is a sectional view taken along the line 2-2 in FIG. 1.

FIGS. 1 and 2 show one particular embodiment of the present invention as it is prepared for use. As shown in these figures, a carrier 10 is provided with a tip 12, a tapered portion 14, and a portion 16 of fixed diameter terminating at a cut-off end 18. The tapered portion 14 extends from the tip 12 to the point 15. The carrier 10 is shown with a gutta percha plug 20 positioned thereon and extending at the rearward end to a plate 22. The plug 20 terminates at a forward end 24 which is located approximately 1.5 mm back from the tip 12. The length of the tapered portion 14 is shown at a. Approximately one-third (a/3) of the tapered length 14 back from the tip 12 is a spherical projection or button 30. This button 30 (one of three) is mounted on the outer surface of the carrier at a distance b from the tip 12. On the fixed-diameter portion of the carrier 10 is a cylindrical tactile collar 32 which tapers outwardly from its point of juncture with the outer surface of the fixed-diameter portion 16 of the carrier 10. The collar 32 serves to provide the user with a tactile indication of that point on the carrier, as well as serving as a stop for the oven arm in the heating of the gutta percha.

As best seen in FIG. 2, the carrier 10 has three spherical bumps or buttons 30 projecting from the outer surface of the carrier 10. In FIG. 2, the diameter of the carrier at the position of the bumps is indicated as CD3. Extending axially along the tapered portion 14 of the carrier 10 is an elongated, shallow groove 40. This groove makes it easier to withdraw the carrier from the gutta percha plug 20. A plate 22 which is slidable along the carrier is placed at the proximal end of the plug 20. When the carrier is to be removed from the root canal after placement of the plug 20, the plate 22 serves to retain the plug 20 in position as the carrier 10 is withdrawn.

As indicated in FIG. 2, the buttons 30 may be located equally spaced about the circumference of the carrier 10 at about 120-degree locations. Alternatively, the buttons 30 may be spaced approximately 90 degrees apart with the center button 30 being on the opposite side of the carrier 10 from the groove 40.

In the views of FIGS. 3, 4 and 5, a carrier 10 having spherical buttons 30 is shown. In this version, the buttons 30 are located at 120 degrees about the periphery of the tapered portion 14. The carrier of the FIG. 3 embodiment has a collar 32 with an adjacent stop plate 22' which is slidable along the carrier 10 to retain the plug in place when the carrier is being withdrawn from the root canal.

Figure 8:
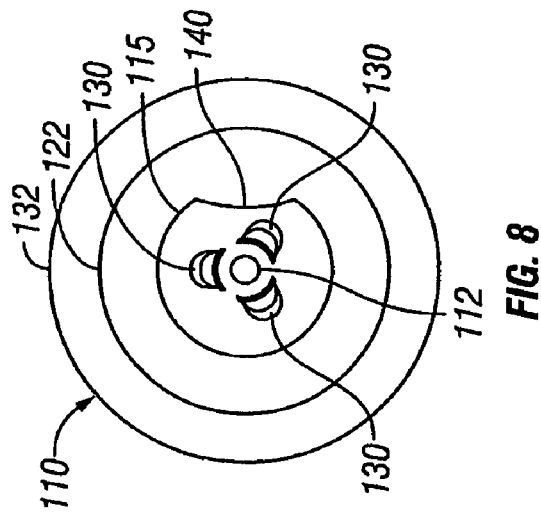
FIG. 8 is a schematic view of the carrier of FIG. 6, viewed from the right-hand end.
Figure 7:
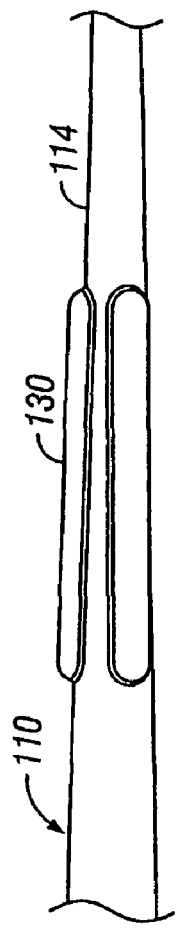
FIG. 7 is an enlarged view of a portion of the carrier of FIG. 6.
Figure 6:
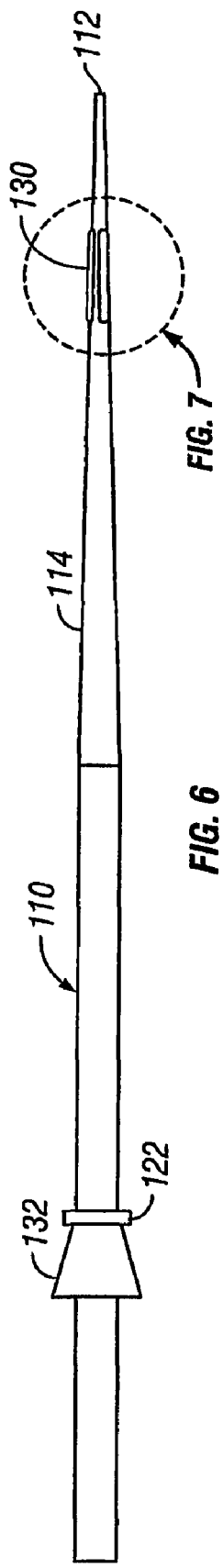
FIG. 6 is a schematic side view of another carrier in accordance with the invention.

FIGS. 6, 7 and 8 depict an alternative embodiment to that of FIGS. 3, 4 and 5. FIGS. 6 and 7 are side views of a carrier 110 having a tapered portion 114, tip 112, tactile element 132 and a retainer plate 122. Instead of the buttons 30 of the first embodiment, this carrier 110 has three elongate longitudinal ridges 130 projecting outwardly from the carrier surface. These longitudinal ridges 130 are rounded in shape and serve the same function as the bumps 30, constituting stops for the carrier 110 when it is being inserted into a root canal with the gutta percha plug 20 mounted on the tapered portion of the carrier. Being elongated, they provide better attachment of the gutta percha plug on the tapered portion of the carrier 110 than is afforded by the bumps 30. Otherwise, the use of the carrier 110 is essentially the same as that of the carrier 10. The carrier 110 also has a shallow groove 140 along one side of the carrier to make it easier to withdraw the carrier from the gutta percha plug.

Figure 11:
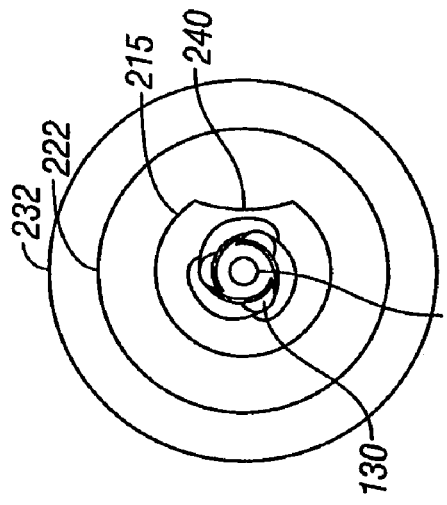
FIG. 11 is a schematic view of the carrier of FIG. 9, viewed from the right-hand end.
Figure 10:
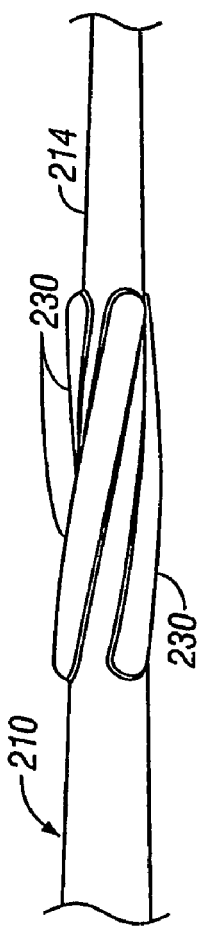
FIG. 10 is an enlarged view of a portion of the carrier of FIG. 9.
Figure 9:
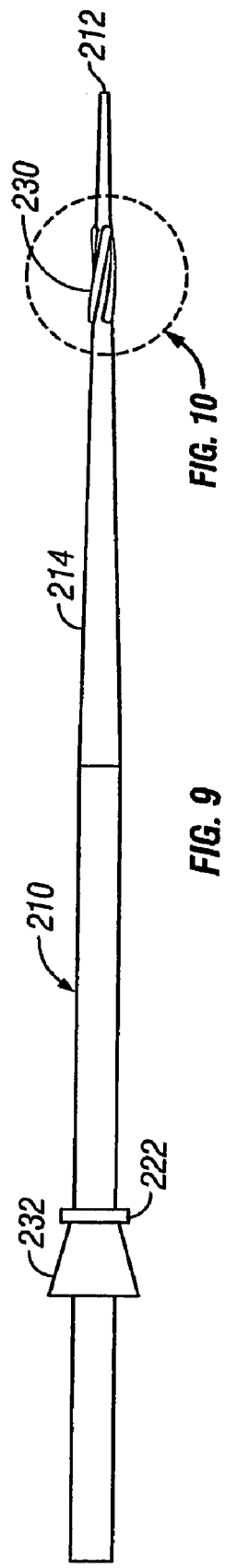
FIG. 9 is a schematic side view of still another carrier in accordance with the invention.

FIGS. 9, 10 and 11 depict still another embodiment of the invention in which a carrier 210 is shown having a tactile collar 232, a tapered portion 214, and a tip 212. Three spiral ridges 230 are positioned along the tapered portion 214 in the same manner as the ridges 130 of the embodiment of FIG. 6, except that these ridges 230 are spiraled slightly. Otherwise, the carrier 21 is essentially identical to the carrier 110 of the FIG. 6 embodiment. Placing the ridges 230 in a spiral configuration gives added holding power for the gutta percha plug on the carrier.

FIGS. 12, 13 and 14 are simulated photographs of the three embodiments of FIGS. 3, 6 and 9, respectively. These views show that the carriers are devoid of a conventional handle which is typically significantly larger in diameter than the diameter of the carrier. Since there is no handle to extend radially from the outer end of the carriers, more carriers can be inserted into a root canal without interference from others. With carriers having conventional handles, at most two carriers can be inserted at a time. With the feature of the present invention providing carriers without handles extending beyond the carrier, as many as four carriers can be inserted into a tooth, one for each root canal, and the outer ends can then all be severed at once.

FIGS. 15A-15B, 16A-16B and 17A-17B are enlarged simulated photographs of the carriers shown in FIGS. 12, 13 and 14, respectively. FIGS. 15, 16 and 17 depict essentially the same elements, designated by the same corresponding reference numerals, as those shown in FIGS. 12, 13 and 14, respectively.

Although there have been described hereinabove various specific arrangements of IMPROVED OBTURATORS in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A dental obturator for inserting filling and sealing material into a previously prepared root canal comprising:
   a rod-like carrier having a fixed-diameter portion joined to a tapered portion at a transition, the rod-like carrier terminating in a pointed tip;
   three or more projections circumferentially spaced on an outer surface on the tapered portion, each projection located a predetermined same distance back from the tip for causing the carrier to bind in the root canal when the tip is a predetermined distance from the canal terminus wherein said projections comprise three or more separate and discrete spherical bumps projecting from the outer surface of the carrier at equally spaced locations about the circumference of the carrier.

2. The dental obturator of claim 1 wherein said predetermined distance from the tip is 3 mm.

3. The dental obturator of claim 1 comprising three spherical bumps projecting from the outer surface of the carrier spaced at 120-degree intervals about the carrier circumference.

4. The dental obturator of claim 1 wherein at least three spherical bumps projecting from the outer surface of the carrier are spaced 120 degrees apart.

5. The dental obturator of claim 1 wherein said projections comprises four spherical bumps projecting from the outer surface of the carrier and there is a gap of 90 degrees between two adjacent bumps and further comprising a shallow groove extending along the carrier in said gap.

6. The dental obturator of claim 1 wherein each of said bumps is a part of a sphere having a diameter which is ¼ the carrier diameter at the location of the bump.

7. The dental obturator of claim 1 wherein each spherical bump is mounted on the outer surface of the carrier such that its center is contiguous with said surface at the point where the bump is located.

8. A dental obturator for inserting filling and sealing material into a previously prepared root canal comprising:
   a rod-like carrier having a fixed-diameter portion joined to a tapered portion at a transition, the rod-like carrier terminating in a pointed tip;
   two or more separate and discrete projections spaced circumferentially on an outer surface on the tapered portion, each separate and discrete projection located a predetermined distance back from the tip, said predetermined distance from the tip for each projection being the same, for causing the carrier to bind in the root canal when the tip is a predetermined distance from the canal terminus
   said dental obturator further including a plug of sealing material surrounding said carrier and extending from a second predetermined distance back from the tip to a point on the fixed-diameter portion which is beyond the transition between the tapered portion and the fixed-diameter portion.

9. The dental obturator of claim 8 wherein the plug of the sealing material is tapered with the same angle of taper as the angle of said tapered portion of the carrier.

10. The dental obturator of claim 8 wherein a forward end of said plug of sealing material is approximately 1.5 mm back from the tip.

11. The dental obturator of claim 8 wherein the sealing material of said plug is gutta percha.

12. The dental obturator of claim 8 wherein the sealing material of said plug is a synthetic polymer.

13. The dental obturator of claim 8 wherein the sealing material of said plug is a bonded resin.

14. A dental obturator for inserting filling and sealing material into a previously prepared root canal comprising:
   a rod-like carrier having a fixed-diameter portion joined to a tapered portion at a transition, the rod-like carrier terminating in a pointed tip;
   two or more separate and discrete projections circumferentially spaced on an outer surface on the tapered portion located a predetermined distance back from the tip, the predetermined distance for each separate and discrete projection being the same, for causing the carrier to bind in the root canal when the tip is a predetermined distance from the canal terminus wherein the carrier further includes an outwardly projecting collar member in the shape of a truncated cone along the fixed diameter portion of the carrier to support the carrier in the holding arm of a heating oven.

15. The dental obturator of claim 14 further including an extension of the carrier beyond said collar member, said extension being of the same diameter as said fixed-diameter portion to facilitate the placement of one or more dental obturators in a patient's root canal.

16. A dental obturator for inserting filling and sealing material into a previously prepared root canal comprising:
   a rod-like carrier having a fixed-diameter portion joined to a tapered portion which terminates in the pointed tip;

at least one projection on the surface on the tapered portion located a predetermined distance back from the tip for causing the carrier to bind in the root canal when the tip is a predetermined distance from the canal terminus, and a plug of sealing material surrounding said carrier and extending from a second predetermined distance back from the tip to a point on the fixed-diameter portion which is beyond the transition between the tapered portion and the fixed-diameter portion, said carrier being devoid of sealing material for a predetermined distance from the tip.

17. The dental obturator of claim 16 wherein said predetermined distance from the tip that is devoid of sealing material is in a range from 0.5 to 3 mm.

18. The dental obturator of claim 16 wherein said predetermined distance from the tip that is devoid of sealing material is 1.5 mm.

* * * * *